(12) United States Patent
Koh et al.

(10) Patent No.: US 7,672,729 B2
(45) Date of Patent: Mar. 2, 2010

(54) MULTI-VARIABLE FEEDBACK CONTROL OF STIMULATION FOR INSPIRATORY FACILITATION

(75) Inventors: Steve Koh, South Pasadena, CA (US); Michael E. Benser, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 437 days.

(21) Appl. No.: 11/624,106

(22) Filed: Jan. 17, 2007

(65) Prior Publication Data

US 2007/0156199 A1 Jul. 5, 2007

Related U.S. Application Data

(62) Division of application No. 10/938,114, filed on Sep. 10, 2004, now abandoned.

(51) Int. Cl.
*A61N 1/36* (2006.01)
(52) U.S. Cl. .................. 607/42; 607/1; 607/2; 607/11; 607/18; 607/19; 607/20; 607/62; 607/115; 600/529; 600/546
(58) Field of Classification Search ................. 607/1–2, 607/11, 18–20, 42, 62, 115; 600/529, 546
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,827,935 A | 5/1989 | Geddes et al. | |
| 4,830,008 A * | 5/1989 | Meer ............................ | 607/42 |
| 4,940,052 A | 7/1990 | Mann et al. | |
| 4,944,298 A | 7/1990 | Sholder | |
| 5,101,824 A | 4/1992 | Lekholm | |
| 5,423,327 A | 6/1995 | Clauson et al. | |
| 5,466,254 A | 11/1995 | Helland | |
| 5,476,483 A | 12/1995 | Bornzin et al. | |
| 5,540,732 A | 7/1996 | Testerman | |
| 5,857,460 A | 1/1999 | Popitz | |
| 6,132,384 A * | 10/2000 | Christopherson et al. ... | 600/529 |
| 6,240,316 B1 | 5/2001 | Richmond et al. | |
| 6,269,269 B1 | 7/2001 | Ottenhoff et al. | |
| 6,314,323 B1 | 11/2001 | Ekwall | |

(Continued)

FOREIGN PATENT DOCUMENTS

EP 1393773 A1 3/2004

(Continued)

OTHER PUBLICATIONS

Hey, E.N. et al., "Effects of Various Respiratory Stimuli on the Depth and Frequency of Breathing in Man," Respir. Physiology (1966) 1: 193-205.

(Continued)

*Primary Examiner*—Carl H Layno
*Assistant Examiner*—Deborah Malamud

(57) ABSTRACT

An exemplary method includes delivering stimulation according to one or more stimulation parameters to cause contraction of the diaphragm, monitoring chest activity related to respiration and, in response to the monitoring, adjusting one or more of the one or more stimulation parameters during contraction of the diaphragm and continuing the delivering. Various other exemplary methods, devices, systems, etc., are also disclosed.

16 Claims, 14 Drawing Sheets

U.S. PATENT DOCUMENTS

| | | |
|---|---|---|
| 6,415,183 B1 | 7/2002 | Scheiner et al. |
| 2002/0072781 A1 | 6/2002 | Lattner et al. |
| 2003/0153953 A1 | 8/2003 | Park et al. |
| 2003/0195571 A1 | 10/2003 | Burnes et al. |
| 2004/0134496 A1 | 7/2004 | Cho et al. |
| 2004/0210261 A1 | 10/2004 | King et al. |
| 2004/0210268 A1 | 10/2004 | Stubbs |

FOREIGN PATENT DOCUMENTS

| | | |
|---|---|---|
| EP | 1393773 B1 | 10/2006 |
| WO | 8600234 | 1/1986 |
| WO | 0141868 A1 | 6/2001 |

OTHER PUBLICATIONS

Wiβkirchen, et al., "Zentrales Schlafapnoe Syndrom und Periodische Atmung," Ther Umsch. (Jul. 2000), vol. 57, No. 7, pp. 458-462. (In German).

NonFinal Office Action, mailed May 12, 2006: U.S. Appl. No. 10/938,114.

Final Office Action, mailed Oct. 16, 2006: U.S. Appl. No. 10/938,114.

* cited by examiner

Approximate Anatomical Diagram

EXEMPLARY DISCRETE FOUR POINT FUNCTION
800

$P_1(F,V)$ $P_2(F,V)$ $P_3(F,V)$ $P_4(F,V)$ $P_{NEW}(F,V)$

EXEMPLARY CONTROL SCENARIOS 1300

MULTI-VARIABLE FEEDBACK CONTROL OF STIMULATION FOR INSPIRATORY FACILITATION

RELATED APPLICATIONS

This application is a division of U.S. patent application Ser. No. 10/938,114, filed Sep. 10, 2004, titled "Multi-variable "Feedback Control of Stimulation For Inspiratory Facilitation," which is related to U.S. patent application Ser. No. 10/769,568, filed Jan. 30, 2004, titled "Inspiratory and/or Expiratory Control Using Chemical and/or Mechanical Drive."

TECHNICAL FIELD

Subject matter presented herein generally relates to therapies to treat respiratory issues wherein the therapies include artificial diaphragm activation.

BACKGROUND

Intrinsic respiration depends on occurrence of many events during a respiratory cycle. Replication of all of these events by an in vivo device is impractical. Indeed, conventional methods for artificial activation of the diaphragm typically rely on a fixed set of parameters that is known to stimulate the phrenic nerve and cause abrupt inspiration. As such these attempts at in vivo activation of the diaphragm to achieve or augment respiration have met with limited success in their ability to mimic intrinsic respiration. Consequently, a need exists for techniques that can more closely mimic intrinsic respiration or achieve more desirable respiration. Various methods, devices, systems, etc., disclosed herein aim to address this need and/or other needs.

SUMMARY

An exemplary method includes delivering stimulation according to one or more stimulation parameters to cause contraction of the diaphragm, monitoring chest activity related to respiration and, in response to the monitoring, adjusting one or more of the one or more stimulation parameters during contraction of the diaphragm and continuing the delivering. Various other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

Overview

Artificial or applied diaphragm activation may be achieved via phrenic nerve stimulation, diaphragm stimulation and/or other tissue stimulation. Artificial or applied diaphragm activation can augment and/or act as a replacement to intrinsic means of diaphragm activation. As described herein, such applied diaphragm activation may be adjusted in a given parameter space or dimension to more closely mimic intrinsic inspiration and/or an inspiratory target. Further, a variety of targets may exist for a given patient wherein each target corresponds to a particular activity. Various exemplary methods, devices, systems, etc., optionally use or include feedback or closed-loop control in an effort to control inspiration. Various exemplary methods, devices, systems, etc., optionally learn over time and may use learned information to discriminate normal inspiration and/or changes in patient state.

Exemplary Stimulation Device

The techniques described below are intended to be implemented in connection with any stimulation device that is configured or configurable to stimulate nerves, stimulate muscle tissue and/or stimulate and/or shock a patient's heart (e.g., myocardial muscle tissue).

Figure 1:
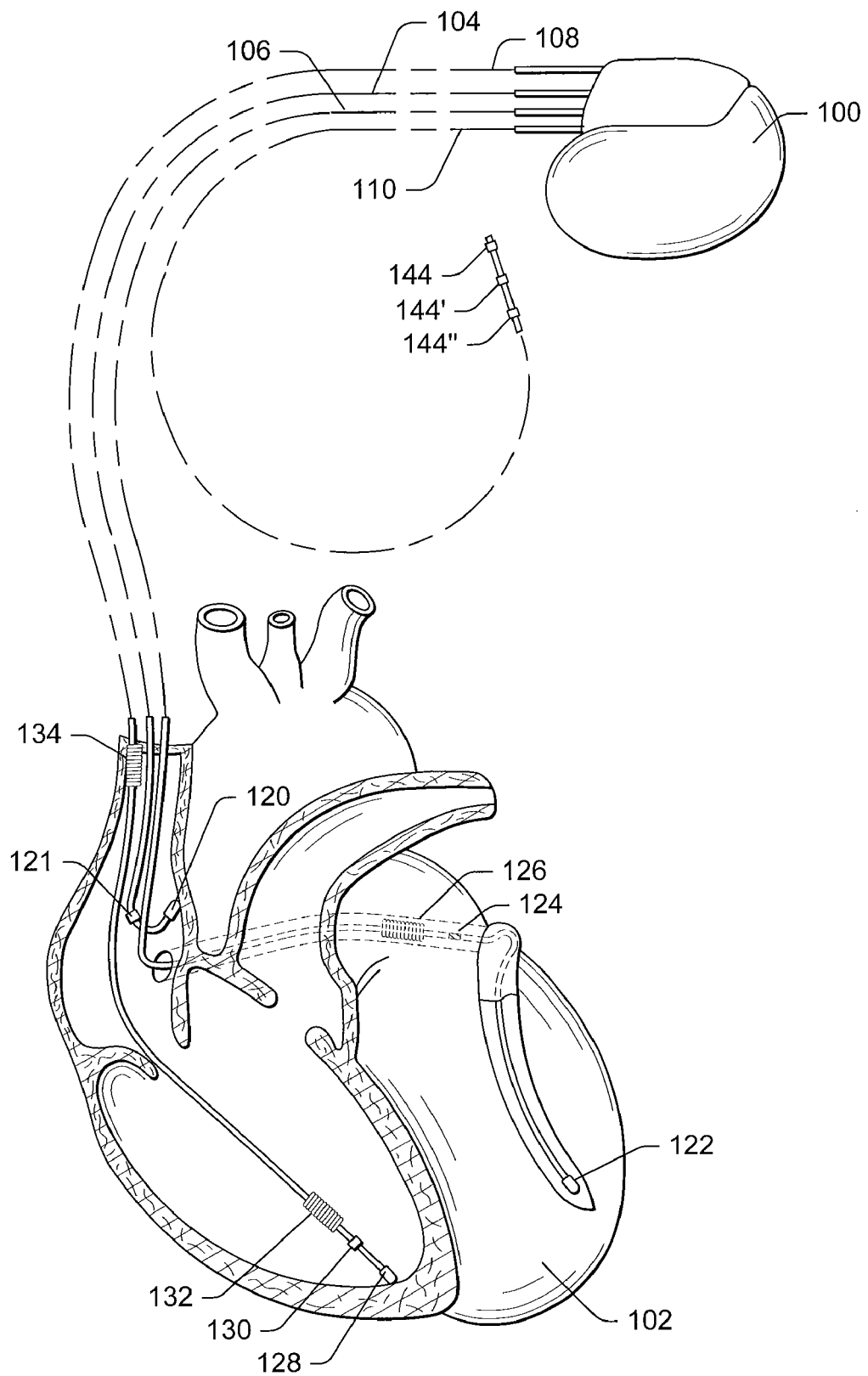
FIG. 1 is a simplified diagram illustrating an exemplary implantable stimulation device in electrical communication with at least three leads implanted into a patient's heart and at least one other lead for delivering stimulation and/or shock therapy. Exemplary devices may have lesser leads as well.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves (e.g., autonomic nerves, phrenic nerves, etc.) and/or muscle tissue other than myocardial tissue. In addition, the device 100 includes a fourth lead 110 having, in this implementation, three electrodes 144, 144', 144" suitable for stimulation of nerves (e.g., autonomic nerves, phrenic nerves, etc.) and/or muscle and/or detection of other physiologic signals that may be used by the implanted system to modify stimulation parameters. The lead 110 may be positioned in and/or near a patient's heart, near a nerve (e.g., an autonomic nerve, a phrenic nerve, etc.) or near muscle tissue other than myocardial tissue within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of nerves and/or muscle tissue.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves, other nerves and/or tissue. Such a lead may include cardiac pacing, nerve and/or muscle stimulation functionality and may further include bifurcations or legs. For example, an exemplary coronary sinus lead includes pacing electrodes capable of delivering pacing pulses to a patient's left ventricle and at least one electrode capable of stimulating a nerve (e.g., autonomic nerve, a phrenic nerve, etc.) and/or other tissue.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating a nerve and/or other tissue; such an electrode may be positioned on the lead or a bifurcation or leg of the lead. For example, an exemplary right ventricular lead includes pacing electrodes capable of delivering pacing pulses to a patient's left ventricle and at least one electrode capable of stimulating a nerve (e.g., autonomic nerve, a phrenic nerve, etc.) and/or other tissue.

Figure 2:
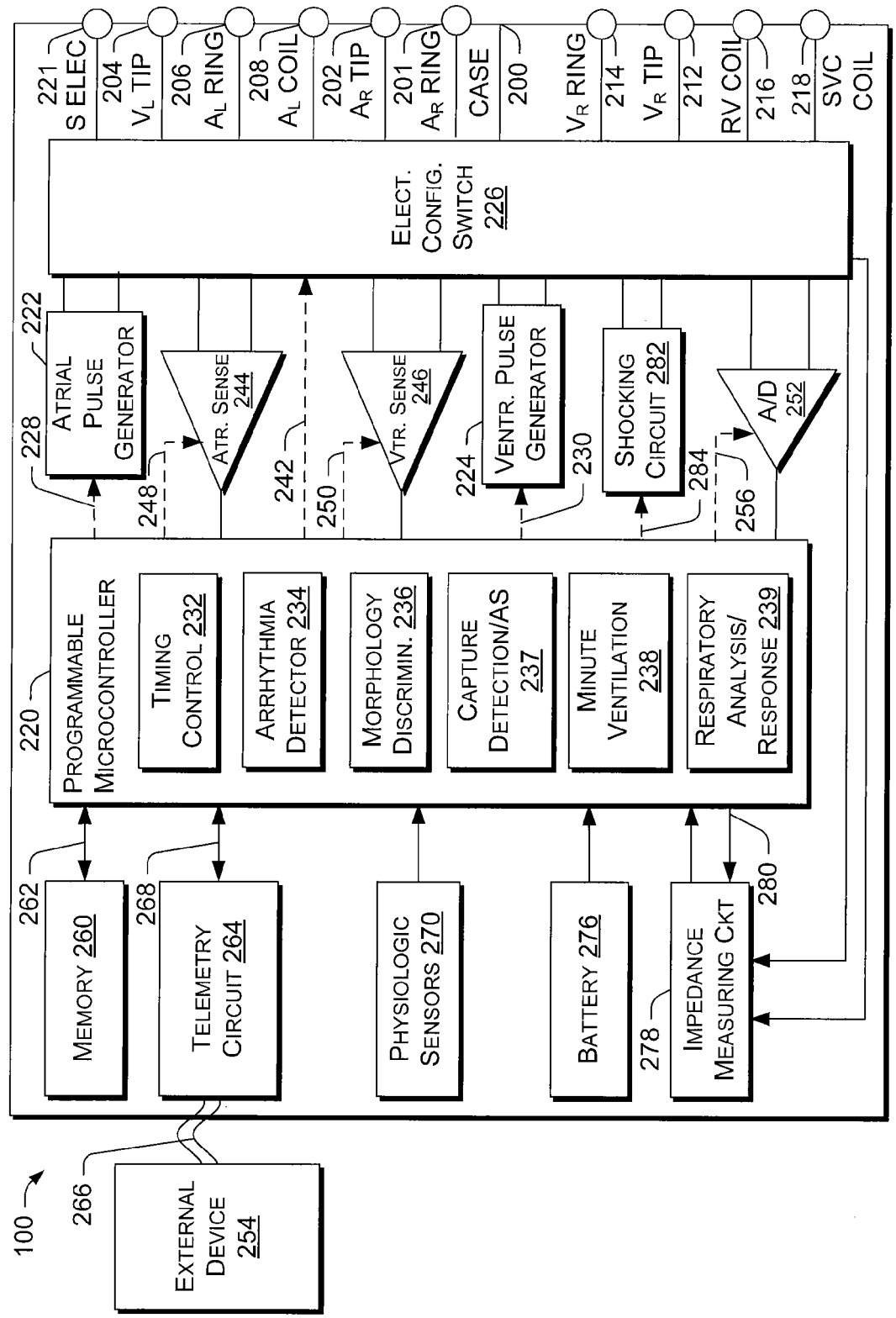
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further optionally configured to measure position and/or movement.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to nerves (e.g., autonomic nerves, phrenic nerves, etc.) and/or muscle tissues. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation and/or treating respiratory issues via cardiac, nerve and/or muscle stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable nerve and/or muscle stimulation electrodes is also possible via these and/or other terminals (e.g., via a stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable nerve and/or muscle stimulation electrodes is also possible via these and/or other terminals (e.g., via the stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to nerves and/or other muscle tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes, for example, an arrhythmia detector 234, a morphology discrimination module 236, a capture detection and/or autosensitivity module 237, a minute ventilation (MV) response module 238 and a respiratory analysis and/or response module 239. These components can be utilized by the stimulation device 100 for determining desirable times to administer various therapies. The aforementioned components may be implemented in hardware as part of the microcontroller 220, or as software/firmware instructions programmed into the device and executed on the microcontroller 220 during certain modes of operation. Various exemplary methods described herein are optionally implemented as logic, which may be embodied in software and/or hardware.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture. The sensing circuits 244, 246, via switches, etc., may also be used to sense information related to respiration (e.g., chest movement monitoring, etc.).

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. Other features for arrhythmia detection, confirmation, etc. are discussed below and may be suitable as appropriate. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Nerve, muscle and/or cardiac signals are also optionally applied to inputs of an analog-to-digital (A/D) data acquisition system 252. The data acquisition system 252 is, for example, configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve and/or muscle stimulation lead through the switch 226 to sample signals across any of desired electrode (e.g., unipolar) or electrodes (e.g., multipolar).

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further includes one or more physiologic sensors 270. For example, a physiologic sensor commonly referred to as a "rate-responsive" sensor is optionally included and used to adjust pacing stimulation rate according to the exercise state of the patient. However, one or more of the physiologic sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, diurnal changes in activity (e.g., detecting sleep and wake states), etc. Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the one or more physiologic sensors 270 may also be external to the stimulation device 100, yet still be implanted within or carried by the patient.

In particular, the one or more physiologic sensors 270 optionally include a position and/or movement sensor mounted within the housing 200 of the stimulation device 100 to detect movement in the patient's position or the patient's position. Such a sensor may operate in conjunction with a position and/or movement analysis module (e.g., executable in conjunction with the microcontroller 220). The position and/or movement sensor may be implemented in many ways. In one particular implementation, the position sensor is implemented as an accelerometer-based sensor capable of measuring acceleration, position, etc. For example, such a sensor may be capable of measuring dynamic acceleration and/or static acceleration. In general, movement of the patient will result in a signal from the accelerometer. For example, such an accelerometer-based sensor can provide a signal to the microcontroller 220 that can be processed to indicate that the patient is undergoing heightened physical exertion, moving directionally upwards or downwards, etc.

Further, depending on position of the implanted device and such a movement sensor, the sensor may measure or monitor chest movement indicative of respiratory characteristics. For example, for a typical implant in the upper chest, upon inspiration, the upper chest expands thereby causing the implanted device to move. Accordingly, upon expiration, the contraction of the upper chest causes the device to move again. Such a movement sensor may sense information capable of distinguishing whether a patient is horizontal, vertical, etc.

While respiratory information may be obtained via the one or more physiologic sensors 270, the aforementioned minute ventilation (MV) sensor 238 may sense respiratory information related to minute ventilation, which is defined as the total volume of air that moves in and out of a patient's lungs in a minute. A typical MV sensor uses thoracic impedance, which is a measure of impedance across the chest cavity wherein lungs filled with air have higher impedance than empty lungs. Thus, upon inhalation, impedance increases; whereas upon exhalation, impedance decreases. Of course, a thoracic impedance may be used to determine tidal volume or measures other than minute ventilation.

With respect to impedance measurement electrode configurations, a right ventricular tip electrode and case electrode may provide current while a right ventricular ring electrode and case electrode may allow for potential sensing. Of course, other configurations and/or arrangements may be used to acquire measurements over other paths (e.g., a superior-inferior path and a left-right path, etc.). Multiple measurements may be used wherein each measurement has a corresponding path.

Direct measurement of phrenic nerve activity may be achieved using a cuff or other suitable electrode appropriately positioned in relationship to a phrenic nerve. For example, a cuff electrode substantially surrounding the right phrenic nerve in the thoracic cavity can detect signals indicative of intrinsic respiratory drive (at least to the right hemidiaphragm). Such signals are typically of amplitude measured in microvolts (e.g., less than approximately 30 microvolts). Sensing may be coordinated with other events, whether natural event or events related to some form of stimulation therapy. As discussed herein, some degree of synchronization may occur between calling for and/or delivering stimulation for diaphragm activation and sensing of neural activity and/or other indicators of respiration and, in particular, inspiration.

While respiratory characteristics are optionally measured with a signal such as a thoracic impedance signal, alternatively or in addition to, central respiratory drive is optionally determined via sensing of phrenic nerve activity. In one example, phrenic nerve (e.g., right and/or left phrenic nerve)

activity is sensed using one or more electrodes on or proximate to the phrenic nerve. In another example, diaphragmatic myopotentials are sensed (e.g., EMG, etc.) using one or more electrodes on or proximate to the diaphragm. Plethysmography may be used in measuring any of a variety of variables that related to respiration.

Other means for detection include measuring the intrathoracic pressure associated with respiration or from stress and/or strain gauges measuring changes in the dimensions of the thoracic cavity including the lungs. Respiratory information may also be inferred by sensing information that relates to mechanisms altered by respiration. For example, body chemistry varies in response to respiration. Hence, chemical parameters such as tissue or blood pH, $PCO_2$, $O_2$, $PO_2$ may be sensed and either used to infer, confirm and/or augment other respiratory information.

Signals generated by the one or more physiologic sensors 270 and/or the MV sensor 238 or impedance sensor are optionally processed by the microcontroller 220 in determining whether to apply one or more therapies.

More specifically, with respect to a movement sensor, the microcontroller 220 may receive a signal from an accelerometer-based sensor that may be processed to produce an acceleration component along a vertical axis (i.e., z-axis signal). This acceleration component may be used to determine whether there is an increased or decreased level of activity in the patient, etc. The microcontroller 220 optionally integrates such a signal over time to produce a velocity component along the vertical direction. The vertical velocity may be used to determine a patient's position/activity aspects as well, such as whether the patient is going upstairs or downstairs. If the patient is going upstairs, the microcontroller 220 may increase the pacing rate or invoke an orthostatic compensator to apply a prescribed stimulation therapy, especially at the onset. If the patient is traversing downstairs, the device might decrease a pacing rate or perhaps invoke the MV response module to control one or more therapies during the descent. The MV response module may provide information to be used in determining a suitable pacing rate by, for example, measuring the thoracic impedance from the MV sensor 238, computing the current MV, and comparing that with a long-term average of MV. As described herein, MV information and/or other sensed information may be used to determine an appropriate respiratory therapy.

The microcontroller 220 can also monitor one or more of the sensor signals for any indication that the patient has moved from a supine position to a prone or upright position. For example, the integrated velocity signal computed from the vertical acceleration component of the sensor data may be used to determine that the patient has just stood up from a chair or sat up in bed. A sudden change in the vertical signal (e.g., a positive change in a direction normal to the surface of the earth), particularly following a prolonged period with little activity while the patient is sleeping or resting, confirms that a posture-changing event occurred. The microcontroller 220 optionally uses this information as one potential condition for deciding whether to invoke, for example, an orthostatic compensator to apply cardiac pacing therapy for treating orthostatic hypotension. Other uses are described in more detail below.

While a two-axis accelerometer may adequately detect tilt with respect to acceleration of gravity, the exemplary stimulation device 100 may also or alternatively be equipped with a GMR (giant magnetoresistance) sensor and circuitry that detects the earth's magnetic fields. Such a GMR sensor and circuitry may be used to ascertain absolute orientation coordinates based on the earth's magnetic fields. The device is thus able to discern a true vertical direction regardless of the patient's position (i.e., whether the patient is lying down or standing up). Where three-axes are measured by various sensors, coordinates may then be taken relative to the absolute orientation coordinates from the GMR. For instance, as a person sits up, the axial coordinates of an accelerometer-based sensor might change by 90°, but the sensor signals may be calibrated as to the true vertical direction based on the output of a GMR sensor and circuitry.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration rate and/or tidal volume ; measuring thoracic or other impedances for determining shock or other thresholds; detecting when the device has been implanted; measuring stroke volume; and detecting the opening of heart valves, etc. The impedance measuring circuit 278 is advantageously coupled to the switch 226 so that any desired electrode may be used.

The impedance measuring circuit 278 may also measure impedance related to lung inflation. Such a circuit may use a case electrode, an electrode positioned in or proximate to the heart and/or another electrode positioned within or proximate to the chest cavity. Various exemplary methods described below rely on impedance measurements to determine lung inflation and/or optionally inspiratory vagal excitation, which can inhibit excitatory signals to various muscles (e.g., diaphragm, external intercostals, etc.).

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the device 100 of FIGS. 1 and 2 has features suitable to call for and/or deliver appropriate diaphragm activation. With respect to calling for diaphragm activation, the respiratory analysis module 239 may be used and with respect to delivery, any of the various pulse generators, electrodes, etc., may be used. In general, diaphragm activation involves direct or indirect phrenic nerve stimulation, transvenous phrenic nerve stimulation and/or direct or indirect diaphragm muscle stimulation.

Direct phrenic nerve stimulation uses one or more electrodes or poles (e.g., magnetic stimulation) in close proximity (e.g., typically in contact with) to a phrenic nerve. Such electrodes or poles may be positioned in the cervical region or other regions of the phrenic nerves which may be superior to the heart, proximate to the heart and/or inferior to the heart, noting that such positioning and/or stimulating may consider risk of parasitic or inadvertent cardiac activation.

Transvenous phrenic nerve stimulation involves positioning one or more electrode or pole in a vessel proximate to a phrenic nerve. For example, the right phrenic nerve runs along the intimal tissue of the superior vena cava and the left phrenic nerve runs near the innominate vein. In general, stimulation energy and power for tranvenous stimulation exceeds that of direct phrenic nerve stimulation. The diaphragm is segmented into approximately two hemidiaphragms; thus, stimulation of a right phrenic nerve may act to activate primarily the right hemidiaphragm while stimulation of a left phrenic nerve may act to activate primarily the left hemidiaphragm. Various studies indicate that an adequate level of respiration may be achieved via activation of a single hemidiaphragm. As described herein, diaphragm activation may involve right and/or left hemidiaphragm activation.

Stimulation of the diaphragm from one or more electrodes or poles positioned proximate to or in the diaphragm may achieve adequate respiration for various purposes disclosed herein. In one example, a pair of electrodes is positioned intramuscularly proximate to the region where a phrenic nerve innervates a hemidiaphragm. In this example, stimulation delivered via the pair of electrodes acts to cause diaphragm activation via nerve and/or muscle excitation. Various studies indicate that inferior placement or positioning of electrodes in or on the diaphragm is suitable to achieve diaphragm activation. Of course, other arrangements may be used where appropriate. Further, an implantable device capable of delivering stimulation for diaphragm activation may be placed subcutaneously in or near the abdomen in a manner that is less invasive than that associated with a pectoral pocket implant.

Figure 3:
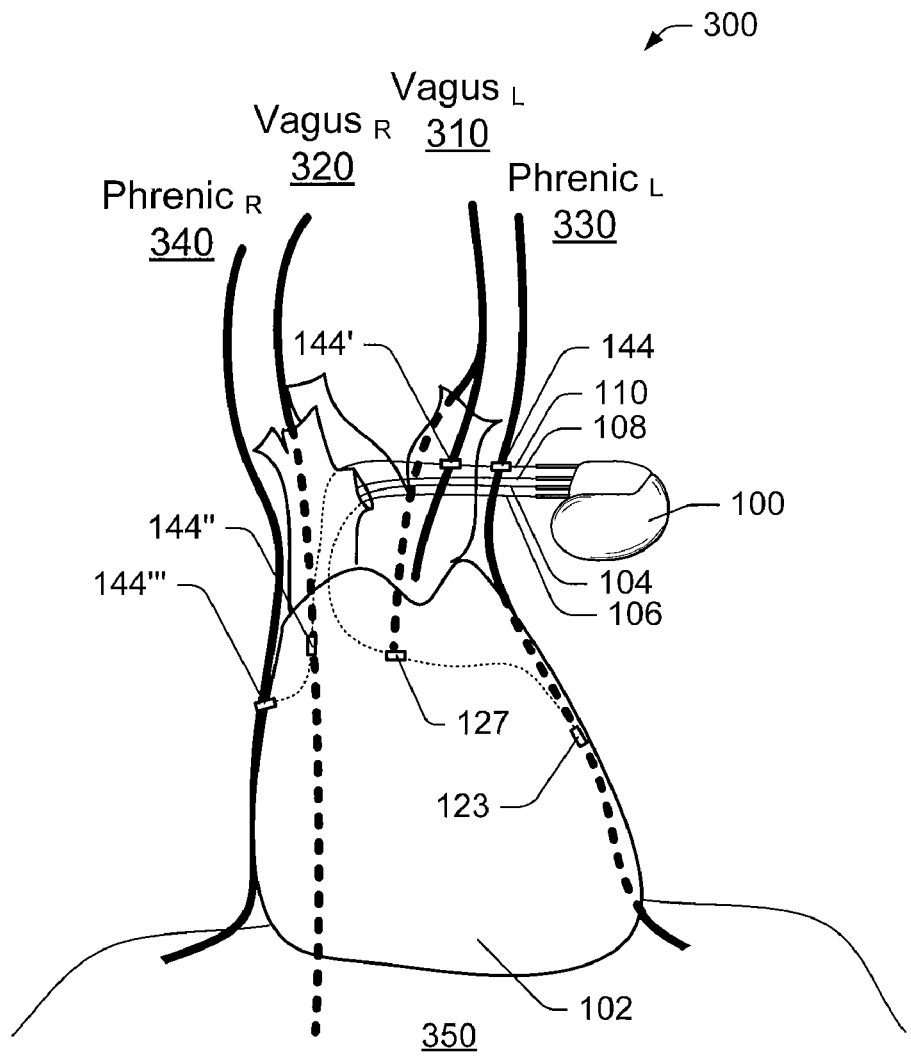
FIG. 3 is an approximate anatomical diagram that includes an exemplary implantable stimulation device capable of implementing some degree of respiratory control.

FIG. 3 shows an approximate anatomical diagram 300 that includes an implanted stimulation device 100. As shown, the left vagus nerve 310 and the right vagus nerve 320 innervate the heart 102 and pass proximate to the heart and the left phrenic nerve 330 and the right phrenic nerve 340 pass proximate to the heart 102.

The implanted stimulation device 100 includes various leads 104, 106, 108, 110, for example, as described with respect to FIG. 1 and FIG. 2. The lead 110 includes an electrode 144 positioned superior to the heart 102 and proximate to the left phrenic nerve 330, an electrode 144' positioned superior to the heart 102 and proximate to the left vagus nerve 310, an electrode 144" positioned posterior to the heart 102 and proximate to the right vagus nerve 320 and an electrode 144''' positioned lateral to the heart 102 and proximate to the right phrenic nerve 340. Thus, via the lead 110, the implanted stimulation device 100 may stimulate either of the vagus nerves 310, 320 and/or either of the phrenic nerves 330, 340.

As shown, the phrenic nerves 330, 340 innervate the diaphragm 350, which is responsible at least in part for respiration, while the vagus nerves 310, 320 innervate various regions of the heart 102 and other regions of the body, noting that all branches and fibers of the various nerves are not shown. As described herein, an implantable device, such as the device 100, is optionally used to activate the diaphragm 350, for example, via phrenic nerve stimulation, diaphragm stimulation and/or other tissue stimulation. Artificial diaphragm activation may augment and/or act as a replacement to intrinsic means of diaphragm activation. An exemplary method may activate the diaphragm 350 using the lead 110, which optionally includes one or more electrodes positioned proximate to or on the diaphragm 350.

The lead 106 of the implanted stimulation device 100 passes transvenously through the right atrium of the heart 102, through the coronary sinus ostium, into the coronary sinus vein and into a surface vein of the heart 102, which is proximate to the left ventricle. The lead 106 includes a distal electrode 123 positioned in a vein on an anterior or lateral surface of the heart 102. In this position, the implanted stimulation device 100 may via the electrode 123 transvenously stimulate the left phrenic nerve 330. As shown in this example, the lead 106 also includes an electrode 127 positioned proximate to the coronary sinus ostium and possibly in the coronary sinus, which traverses the dorsal or posterior surface of the heart 102. The left vagus nerve 310, as described herein, include nerve fibers that innervate a region at or near the position of the electrode 127. This region is sometimes referred to as a "fat pad" and/or a "subplexus". As described further below, such subplexes typically include some degree of autonomic innervation (e.g., sympathetic and/or parasympathetic) which can affect operation of the heart. The implanted stimulation device 100 can stimulate this subplexus and/or fibers of the left vagus nerve 330 via the electrode 127.

In general, the phrenic nerves 330, 340 run from above the subclavian veins and down around the heart 102 (e.g., left and right side) to the surface of diaphragm 350. Various exemplary methods optionally include positioning one or more electrodes at a superior vena cava location and/or a location at right atrial free wall which may be proximate to the right phrenic nerve 340. Stimulation at these sites may generate a profound effect on the phrenic motor nerves that innervate the diaphragm 350 and thereby modulate breathing.

Experimental data show that a bipolar electrode positioned inside SVC was able to stimulate the right phrenic nerve 340 at thresholds of a minimum of approximately 1 volt. Further, a suitable pacing threshold was obtained with a tip electrode directly in contact with a wall of the SVC. To reduce movement of such an electrode, fixation is possible via use of a basket, a screw, RF coagulation, etc., which can reduce risk of dislodging the electrode into the right atrium and right ventricle. For example, if such an electrode were dislodged to the right atrium or right ventricle, it could cause inappropriate sensing and possibly induction of fibrillation via delivery of a phrenic stimulation pulse train (e.g., approximately 20 Hz, etc.).

As shown, the left vagus nerve 310 (or nerve bundle) and the right vagus nerve 320 (or nerve bundle) are part of the Xth cranial nerve and run from the neck down toward the heart. The right vagus nerve 320 runs to the posterior side of the SVC and subclavian vein while the left vagus nerve 310 runs down to the posterior side of the left atrium. Various exemplary methods optionally achieve vagal nerve stimulation via transvenous delivery of energy via electrodes in SVC, subclavian vein, and/or coronary sinus vein.

Depending on electrode location, stimulation parameters, etc., some risk may exist for undesirable myocardial stimulation. Undesirable myocardial stimulation generally includes stimulation that may interfere with proper operation of the heart. For example, delivery of stimulation during a vulnerable period may cause arrhythmia. To avoid undesirable myocardial stimulation and/or to reduce risk associated with any inadvertent myocardial stimulation associated with stimulation of a nerve or other tissue, various exemplary methods, devices, systems, etc., include or can implement timing and/or pacing schemes. For example, an exemplary method includes synchronizing delivery of a nerve stimulation pulse train with the action potential refractory period of a myocardium depolarization, which may be due to a paced and/or an intrinsic event.

In various exemplary methods, devices, systems, etc., phrenic nerve stimulation optionally includes one or more phrenic nerve stimulation pulses delivered during a delivery window formed of a sequence of multiple short pulses applied in rapid succession. Frequency considerations are discussed further below. In general, a pulse having a pulse width of approximately 100 μs is well suited for phrenic nerve stimulation. Pulse widths may fall within a range of approximately 5 μs to approximately 1000 μs.

In general, pulse width and number of short pulses are programmable and may be considered control parameters. Other control parameters include timing, duration, amplitude, frequency, etc. In one example, individual short pulses in a pulse train have a width of approximately 5 μs to approximately 200 μs wherein the number of pulses in a train may vary as appropriate.

While the foregoing discussion mentions phrenic nerve stimulation, the control parameters and concepts may apply to diaphragm activation in general, whether used to augment or as a replacement to intrinsic means of diaphragm activation.

Stimulation for diaphragm activation may use stimulation waveforms such as monophasic, biphasic or of other phase types. For example, an exemplary device may use a biphasic pulse that aims to reduce risk of inappropriate cardiac stimulation. Such a biphasic pulse or biphasic pulse train may be applied in a delivery window that lies outside of a vulnerable window (e.g., where a substantial risk of stimulation induced arrhythmia may exist) and at a time when cardiac stimulation is not desired or desirable. Thus, various exemplary devices, methods, systems, etc., may use pulses that activate the diaphragm only, use pulses that stimulate the heart and activate the diaphragm, use pulses that activate the diaphragm and stimulate a vagal nerve and/or use pulses that activate the diaphragm and stimulate a vagal nerve and the heart. Of course, an exemplary device may have an ability to deliver pulses that stimulate the heart only. Pulse phase, delivery location, timing, duration, energy, phase, etc., may be used as parameters to avoid or to promote diaphragm activation and/or stimulation of a vagus nerve and/or myocardium.

Figure 4:
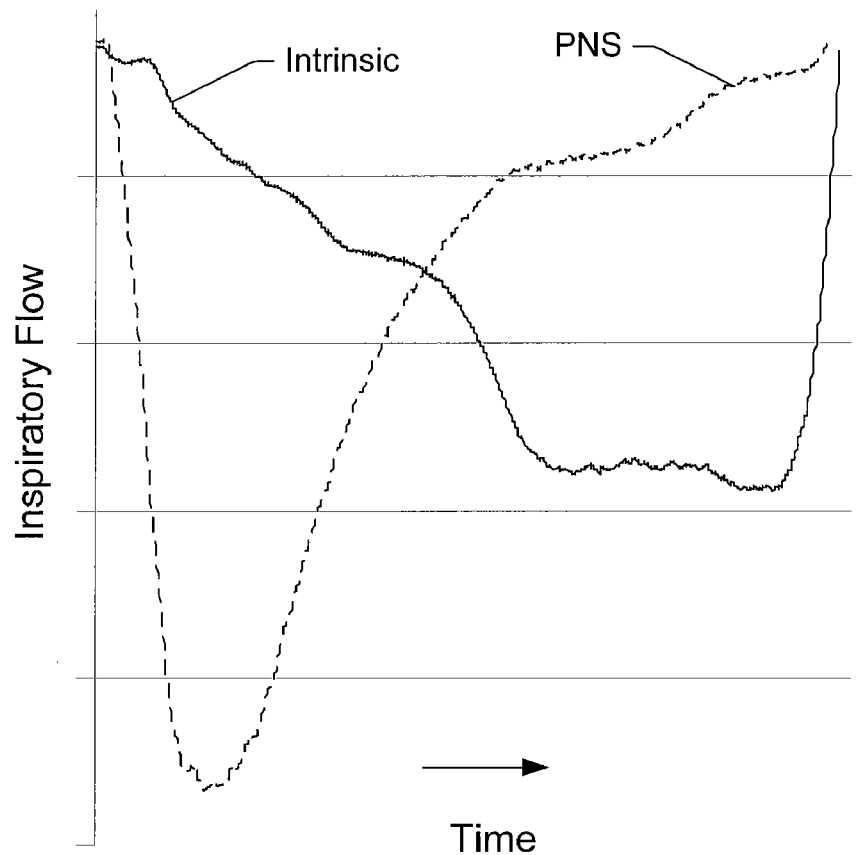
FIG. 4 is a plot of exemplary inspiratory flow patterns from intrinsic and phrenic nerve stimulation (PNS).

FIG. 4 shows a plot 400 of inspiratory flow versus time for inspiration due to intrinsic respiration (e.g., intrinsic activation of the diaphragm) and for inspiration due to applied diaphragm activation. According to the plot 400, intrinsic respiration results in a normal inspiration pattern having a late flow peak whereas the particular form of applied diaphragm activation results in an inspiration pattern having an early flow peak. While the data presented in the plot 400 are only examples, as actual intrinsic or applied stimulation patterns may differ, they serve to exhibit typical differences between intrinsic respiration and respiration associated with applied diaphragm activation.

In the applied activation case, flow increases fairly dramatically after delivery of stimulation. If the upper airway has insufficient patency during this period of increasing flow, the upper airway may collapse. Some studies have identified the oro-pharynx region as the most likely site of airway collapse because of a lack of support by rigid cartilaginous or bony structures such as those present in nasal and laryngeal airways. For example, obstructive sleep apnea (OSA) patients frequently experience airway collapse in the pharyngeal region. OSA is typically associated with normal intrinsic phrenic nerve stimulation and inadequate airway patency, which may be due to excessive tissue around the airway. In contrast to obstructive sleep apnea, central sleep apnea (CSA) is mainly due to an instability of the breathing control system. More specifically, CSA is a breathing disorder characterized by recurrent episodes of central hypopneas or apneas and hyperventilation, which as described by Cheyne and Stokes, may show a crescendo-decrescendo pattern of respiration. Cheyne-Stokes-Respiration (CSR) or periodic breathing is often associated with heart failure and neurological disorders especially those involving the brainstem (see, e.g., Wisskirchen et al., "Central sleep apnea syndrome and Cheyne-Stokes respiration," Ther Umsch. 2000 July; 57(7):458-62).

While the plot 400 shows data for inspiration, knowledge of characteristics of the expiratory part of the respiratory cycle (i.e., expiration) may also be of benefit for applied diaphragm activation. For example, in normal respiration, during early expiration, laryngeal width is typically low while pharyngeal cross-sectional area is typically at a cycle maximum. As expiration continues, an increase typically occurs in laryngeal width and, at the end of expiration, a drop occurs in the pharyngeal cross-sectional area. As such, changes in pharyngeal and/or laryngeal caliber as expiration progresses may possibly be used to determine airway patency for a subsequent inspiration. Further, some degree of applied diaphragm activation may allow for an examination of characteristics of airway patency, which, in turn, may be used to deliver appropriate stimulation for diaphragm activation.

While some exemplary methods, devices, systems, etc., optionally include sensing or monitoring that can detect airway patency or a lack thereof, various exemplary methods, devices, systems, etc., include respiratory control (e.g., inspiratory control and/or expiratory control) that relies on a learned respiratory pattern, a programmed respiratory pattern and/or feedback of sensed respiration. Such exemplary methods, devices, systems, etc., aim to mimic intrinsic respiratory patterns, optionally in a manner that prevents or reduces risk of airway collapse.

Figure 5:
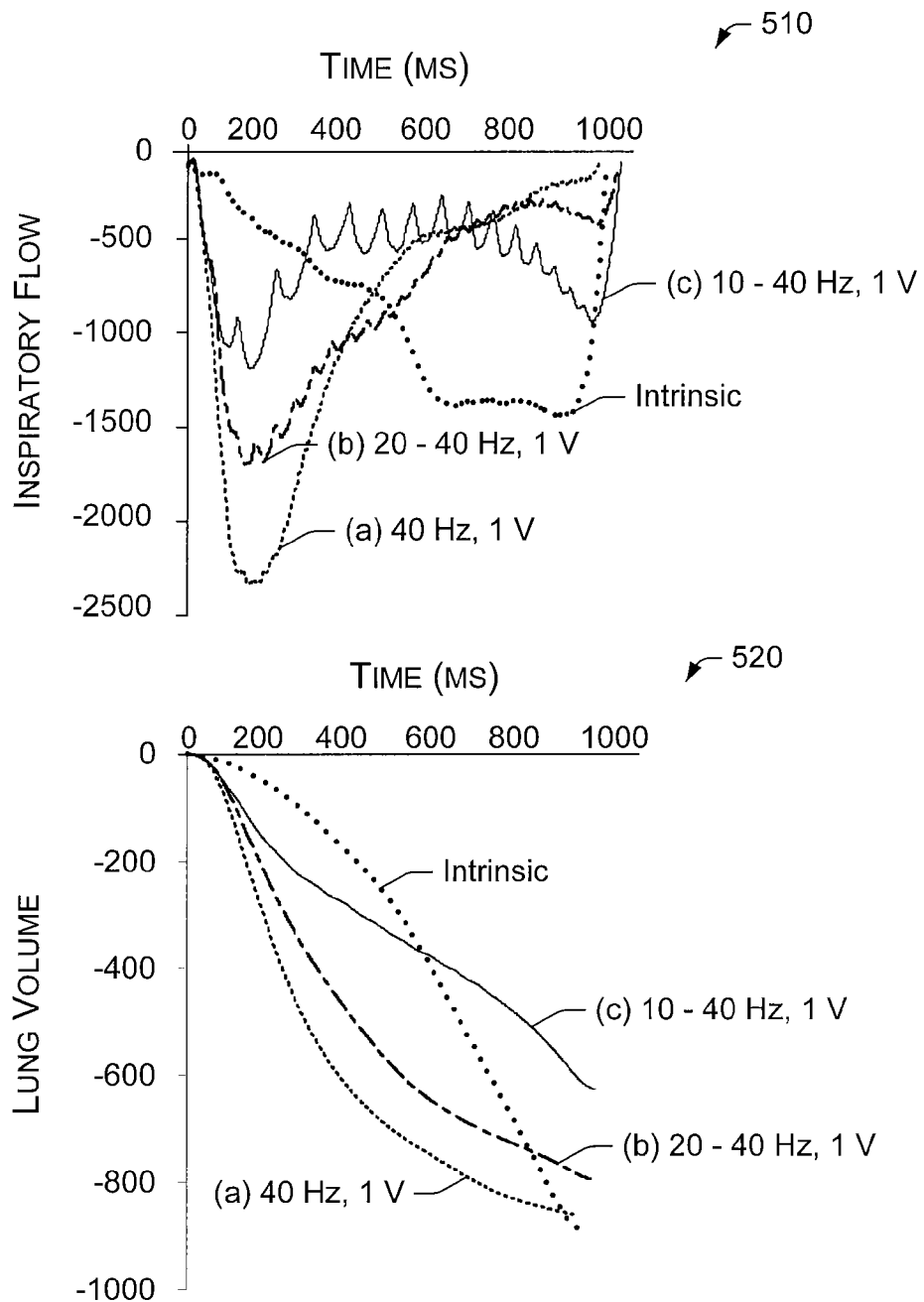
FIG. 5 is a series of plots that include data of inspiratory flow and lung volume versus time for stimulation delivered using a variety of stimulation parameters.

FIG. 5 shows exemplary scenarios 500 in a series of plots 510, 520. The plot 510 includes data for inspiratory flow versus time and the plot 520 includes corresponding data for lung volume versus time. The two plots 510, 520 include data for intrinsic inspiration, applied diaphragm activation using (a) phrenic nerve stimulation at approximately 40 Hz and approximately 1V, (b) applied phrenic nerve stimulation at approximately 20 Hz to approximately 40 Hz and approximately 1V, and (c) applied phrenic nerve stimulation at approximately 10 Hz to approximately 40 Hz and approximately 1V.

According to the data of the two plots 510, 520, some degree of error exists between intrinsic inspiration data and applied diaphragm activation inspiration data. In particular, the plot 520 indicates that the error between the lung volume data for intrinsic inspiration and the lung volume data for inspiration for applied diaphragm activation via phrenic nerve stimulation is at a minimum for applied phrenic nerve stimulation parameters of approximately 10 Hz to approximately 40 Hz and approximately 1V. Thus, error between intrinsic inspiration and inspiration due at least in part to applied diaphragm activation can be controlled via stimulation parameters such as frequency, etc.

As described herein, an exemplary method may include controlling inspiration for a set number of inspirations using a closed-loop controller that relies on one or more adjustable stimulation parameters, recording values for the one or more adjustable parameters, determining an average value for each of the one or more adjustable parameters and controlling inspiration based at least in part on the average value for each of the one or more adjustable parameters. Such an exemplary method optionally uses stimulation that includes a waveform having a plurality of frequency components and where each of the frequency components optionally has a frequency greater than approximately 1 Hz and/or less than approximately 50 Hz.

Figure 6:
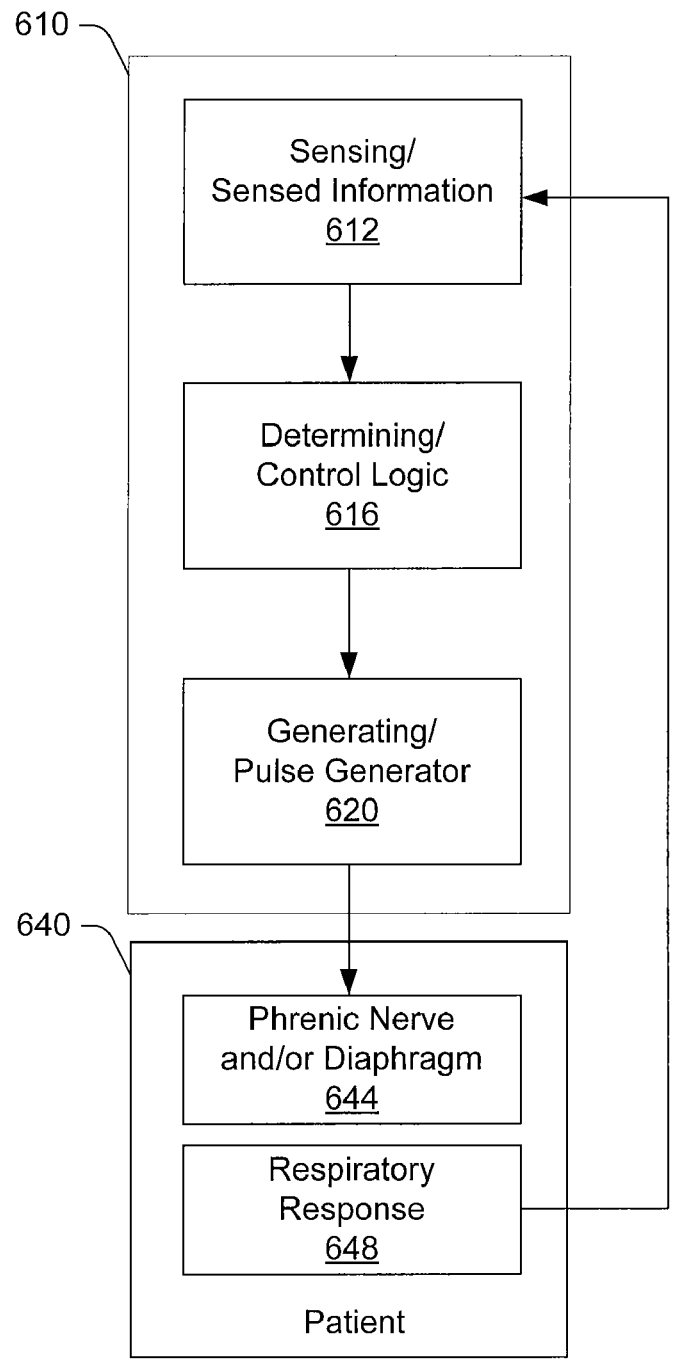
FIG. 6 is a block diagram of an exemplary closed-loop control method, device and/or system.

FIG. 6 shows an exemplary closed-loop control method, device and/or system 600. For example, as an exemplary closed-loop method 610, sensing 612, determining 616 and generating 620 functions occur that aim to control respiration of a patient 640; as an exemplary device 610, sensed information 612 (e.g., an input, a sensor, etc.), control logic 616 (e.g., operable using hardware and/or software) and a pulse generator 620 can operate to control respiration; and, as an exemplary system 610, sensed information 612 acquired using one or more local or remote sensors, control logic 616 including local or remote hardware and/or software, and a pulse generator 616 that includes one or more leads and/or electrodes capable of delivering stimulation to a nerve, a muscle, etc., operate to control respiration. As shown, the block 610 operates in conjunction with a patient 640 wherein the pulse generator 620 aims to activate the diaphragm via stimulation of a phrenic nerve and/or the diaphragm 644, which, in turn, causes a respiratory response 648. In general, sensed information 612 stems from the respiratory response 648 or lack thereof. Hence, feedback or closed-loop control of respiration (e.g., inspiration and/or expiration, etc.) is achieved.

Figure 7:
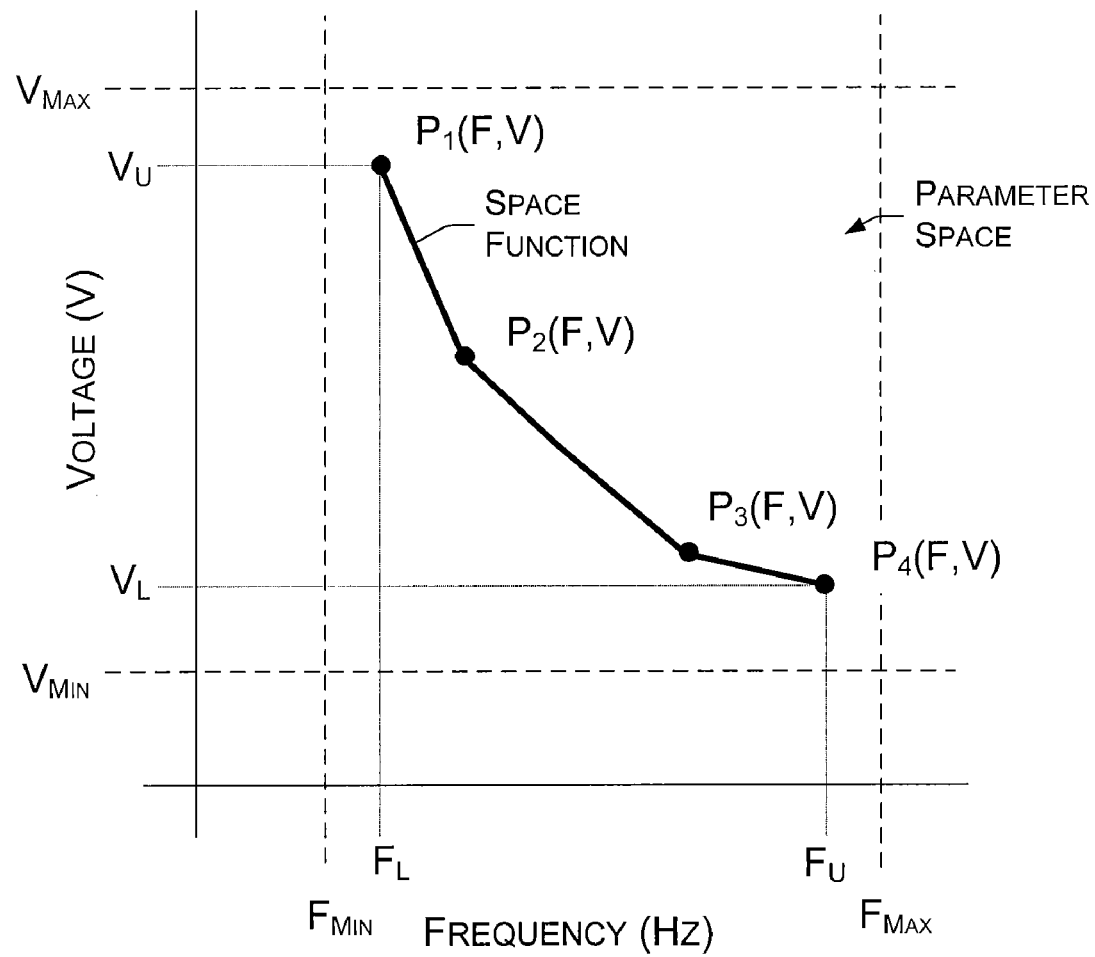
FIG. 7 is a plot of an exemplary control function in a frequency and voltage parameter space.

FIG. 7 shows an exemplary function 700 of voltage versus frequency. The exemplary function 700 exists in a parameter space that includes at least voltage and frequency. Of course, in other examples, a function may depend on current, power, duty cycle, pulse width, etc., in addition to or as alternatives to voltage and/or frequency. Further, a function may depend on time, respiratory patterns, patient activity, etc.

The exemplary function 700 is typically at least a part of control logic that determines one or more pulse generation or stimulation parameters, for example, based on sensed information, programmed information, etc. The particular function shows four points $P_1$, $P_2$, $P_3$ and $P_4$, which depend on frequency and voltage. The four points lie within a parameter space defined by a minimum voltage, a minimum frequency, a maximum voltage, and a maximum frequency. The four points of the function lie within a subspace defined by a lower voltage ($V_L$), a lower frequency ($F_L$), an upper voltage ($V_U$), and an upper frequency ($F_U$). In one example, all four points are used to generate stimulation whereas in another example, a progression occurs to cause inspiration wherein $P_1$, $P_2$, $P_3$ and $P_4$ represent an event-dependent (e.g., time or other event) sequence of stimulation parameters that are used over the course of stimulation.

Figure 8:
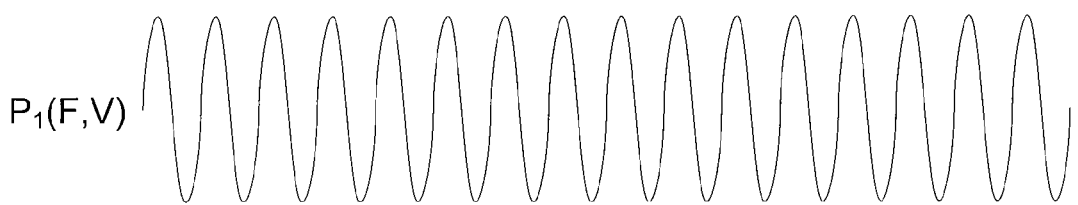
FIG. 8 is a series of waveforms corresponding approximately to the exemplary control function of the plot of FIG. 7.
Figure 8:
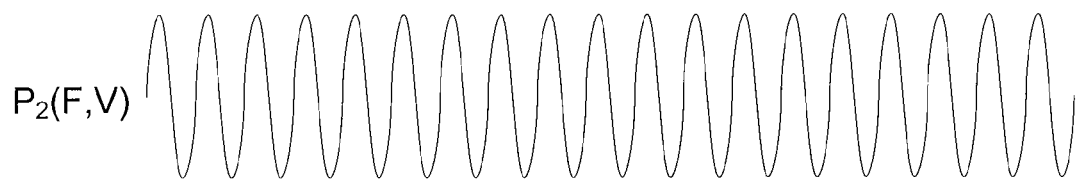
Figure 8:
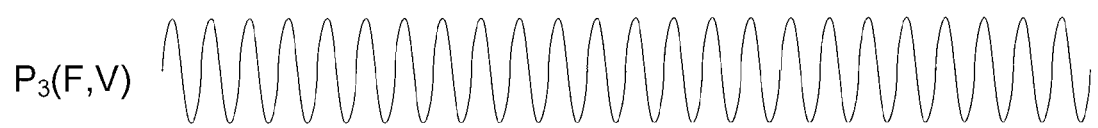
Figure 8:
Figure 8:
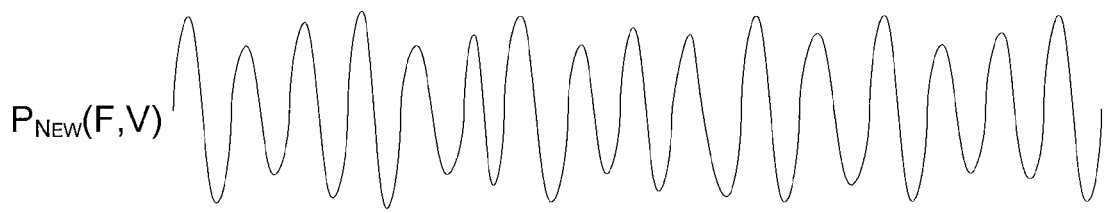

FIG. 8 shows a representation of stimulation waveforms 800 for the example where all four points are used to generate stimulation. A first waveform corresponds to $P_1$ (e.g., having a high voltage and a low frequency), a second waveform corresponds to $P_2$, a third waveform corresponds to $P_3$, a fourth waveform corresponds to $P_4$ (e.g., having a low voltage and a high frequency) and a fifth waveform $P_{New}$ corresponds to a new waveform that may depend to some extent on another waveform (e.g., a prior waveform).

With respect to the data presented in FIG. 5, the four points $P_1$-$P_4$ optionally correspond to frequencies ranging from approximately 10 Hz to approximately 40 Hz. This particular combination of frequencies has been shown to be capable of achieving inspiratory flow and lung volume over time that mimics intrinsic inspiration. Accordingly, an exemplary method includes determining a combination of stimulation frequencies that aim to achieve a desired respiratory response. Control logic for making such a determination optionally includes programmed information based on previous stimulation results performed by an implanted device and/or previous stimulation results performed through use of some other type of stimulation device (e.g., external, partially external, etc.).

An exemplary method may rely on error between inspiration due to applied diaphragm activation and a desired inspiration profile (e.g., model, measured, etc.). With respect to the waveforms $P_1$-$P_4$ of FIG. 8, each may have a corresponding error: $\epsilon_1$-$\epsilon_4$. Such an exemplary method may rely on the following equation (Eqn. 1) in arriving at $P_{New}$:

$$P_{New}(F_N, V_N) = \Sigma[\epsilon_i^{-1} * P_i(F_i, V_i)]/\Sigma \epsilon_i^{-1} \qquad (1)$$

According to Eqn. 1, the index "i" may vary as appropriate where i>1. Other manners of accounting for error may be used to arrive at a new parameter or parameters for diaphragm activation.

An exemplary method may detect error between a measured and an "ideal" impedance profile and then rely on such error to improve respiration by adaptively adjusting one or more stimulation parameters. Errors are optionally recorded with respect to time and forgetting factors are optionally used to weight errors.

Figure 9:
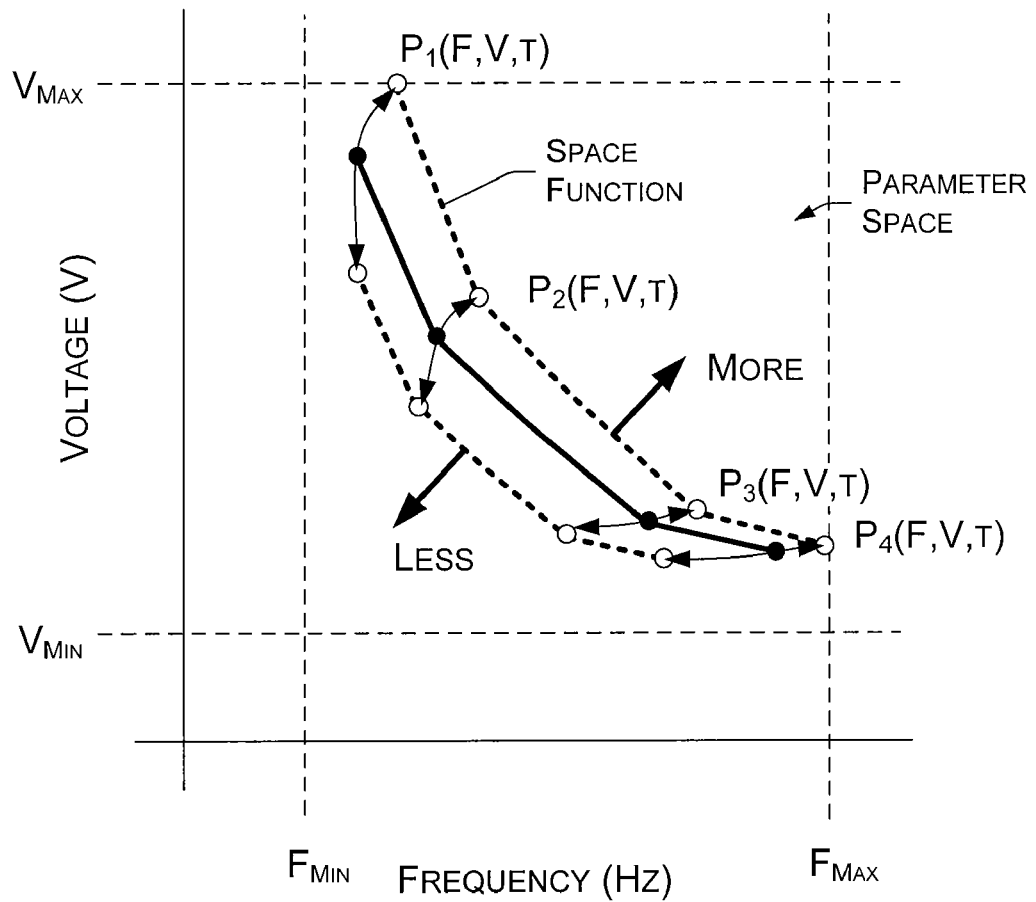
FIG. 9 is a plot of various exemplary control functions with respect to time in a frequency and voltage parameter space.

FIG. 9 shows an exemplary function 900 of frequency and voltage with respect to time. In this example, the various points may vary with respect to time, for example, in response to sensed information related to respiration. If an analysis of sensed information determines that more inspiratory flow, lung volume, etc., is desired, then one or more of the points may increase in voltage and/or frequency, as illustrated by an arrow labeled "more". Whereas, if such an analysis determines that less inspiratory flow, lung volume, etc., is desired, then one or more of the points may decrease in voltage and/or frequency, as illustrated by an arrow labeled "less". Of course, to achieve a desired level of inspiration, one or more points may increase while one or more other points decrease in frequency and/or voltage.

Figure 10:
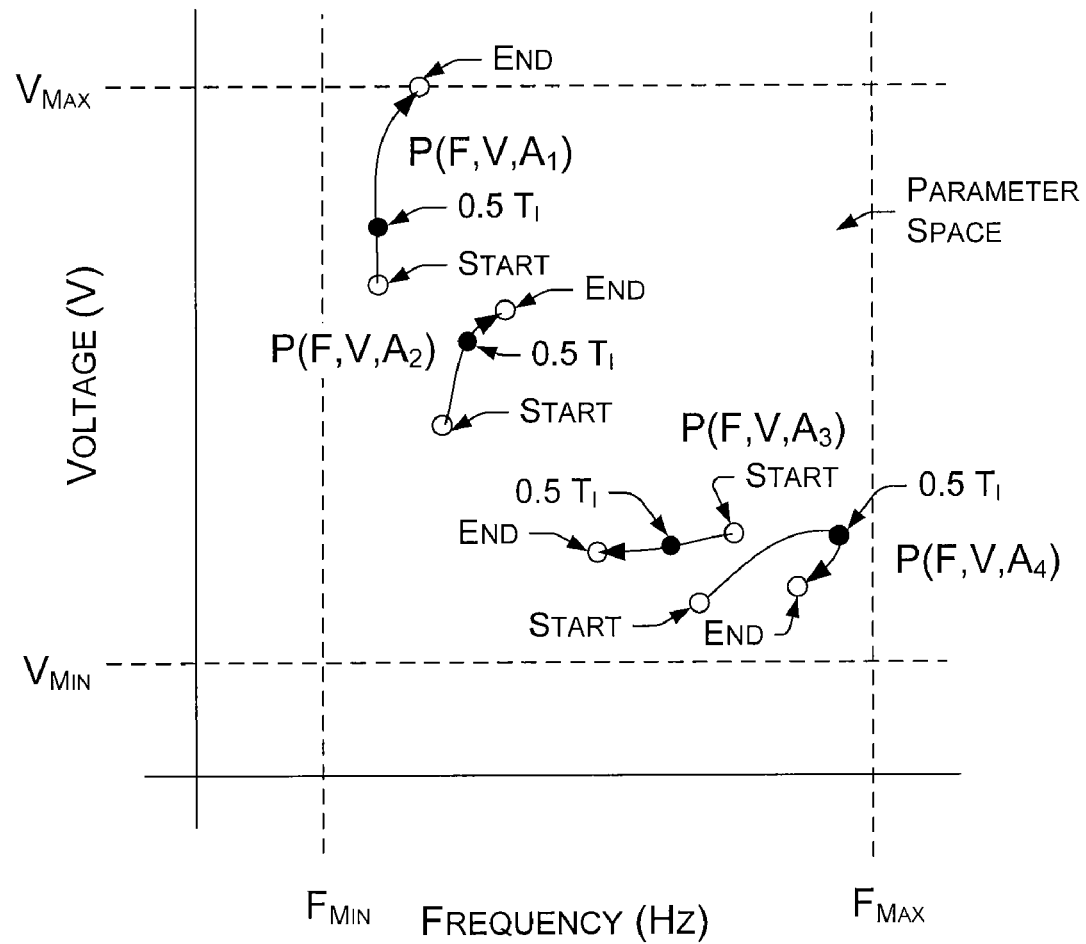
FIG. 10 is a plot of various exemplary control functions with respect to activity in a frequency and voltage parameter space.

FIG. 10 shows various exemplary functions 1000 of frequency and voltage with respect to time and/or activity. For example, the four functions may correspond to four different activities, such as sleep ($A_4$), sitting ($A_3$), standing ($A_2$) and exercising ($A_1$). Hence, an exemplary implantable device optionally includes one or more stimulation functions wherein each function corresponds to a different activity state of a patient. The four functions are shown along with exemplary mid-points 0.5 $T_I$, where $T_I$ is an inspiration time for a corresponding function or activity. Functions for activities $A_1$ and $A_2$ indicate an increase in duty cycle and/or power over inspiration time while the function for activity $A_3$ indicates a decrease in duty cycle and/or power over inspiration time. The function for activity $A_4$ indicates stimulation parameters calling for a maximum in duty cycle and/or power at approximately 0.5 $T_I$. Thus, in the exemplary functions 1000, stimulation optionally has a single frequency value and/or a single voltage value at any given point in time during stimulation assisted inspiration.

Figure 11:
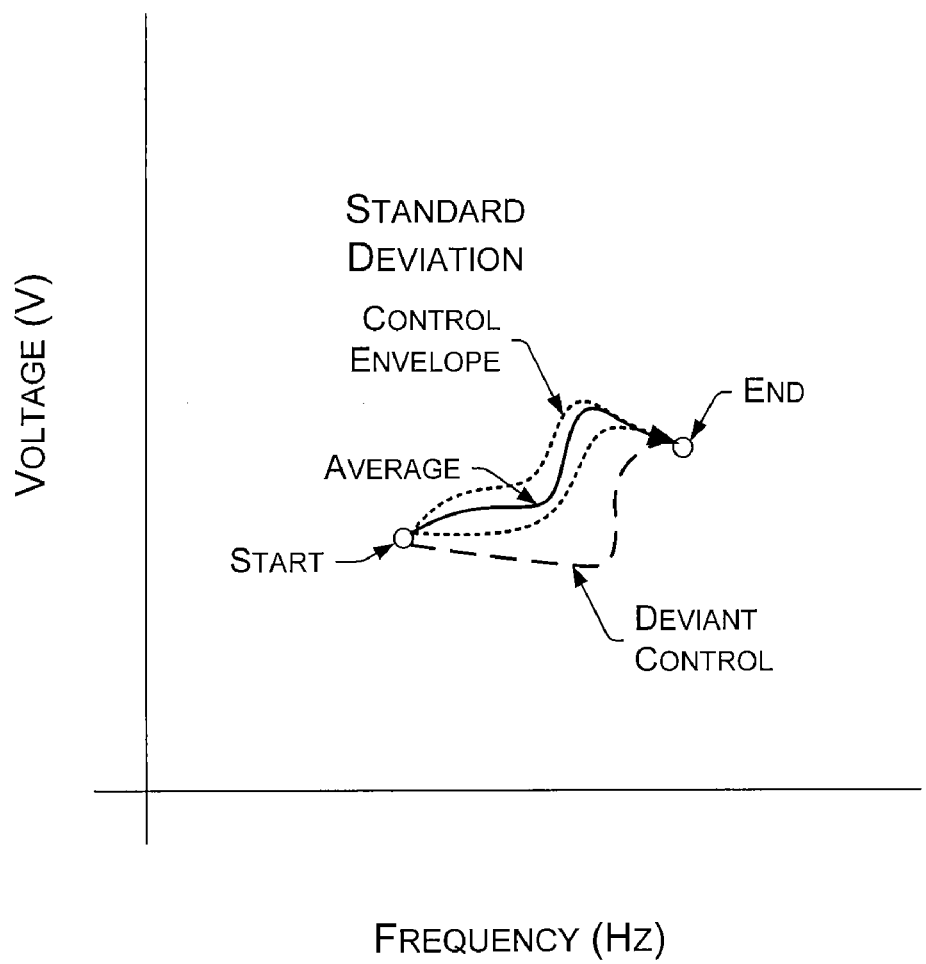
FIG. 11 is a plot of an exemplary control function and a corresponding control envelope in a frequency and voltage parameter space.

FIG. 11 shows an exemplary control function 1100 for control of respiration (e.g., inspiration). The exemplary function 1100 traces a voltage and frequency path with respect to time. A solid line represents an average path or set of parameters achieved via feedback control or closed-loop control of inspiration. For example, the average path may represent an average of a selected number of controlled inspirations (e.g., 2, 7, 20, etc.). A statistical analysis may further determine paths representing upper and/or lower limits, based on standard deviations, etc. Over some period of time and/or number of controlled inspirations, an envelope of "normal" paths may be determined and if a deviant path occurs, this event may be registered in memory of an implantable device to indicate a potential change in patient state. Such a change in state may be a health related state, an activity state, etc. As such, feedback or closed-loop control may be used to indicate changes in patient state.

Figure 12:
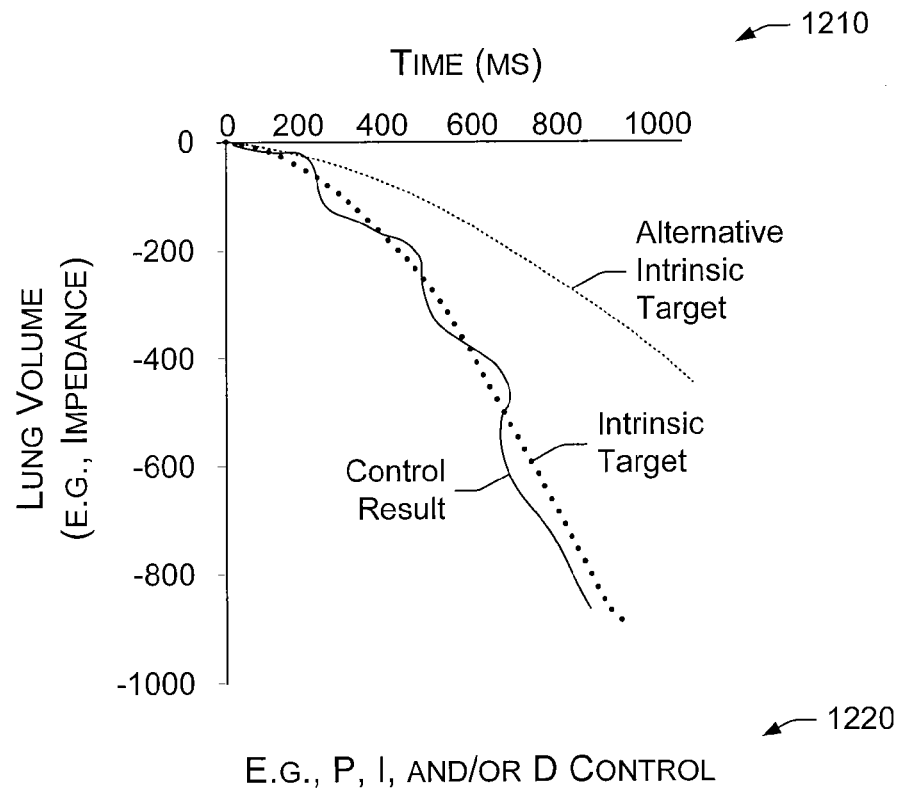
FIG. 12 is a series of plots of an exemplary control scheme that includes an intrinsic target and changes in power that aim to minimize error between information related to actual inspiration and the intrinsic target.
Figure 12:
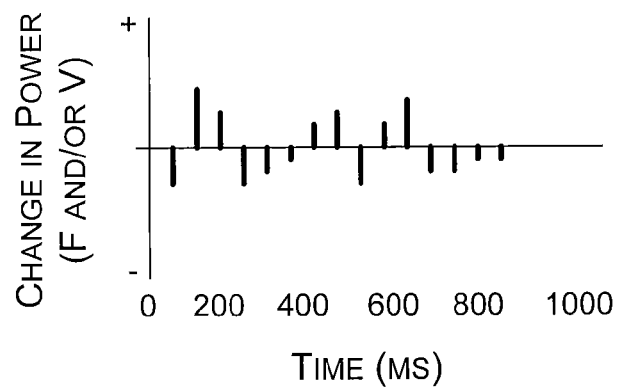

FIG. 12 shows an exemplary control scheme 1200. A plot 1210 of lung volume versus time includes an intrinsic target, an alternative intrinsic target and a control result. According to such an exemplary scheme, lung volume may be acquired through use of a sensor (e.g., impedance, etc.) that provides sensed information related to lung volume. The intrinsic target and the alternative intrinsic target paths optionally correspond to different activity states for a given patient. Control logic optionally includes one or more targets such as an intrinsic target which may be used in a control logic algorithm (e.g., proportional, integral, derivative, etc.).

According to a plot 1220 of change in power (or frequency and/or voltage) versus time, sensed information is used by control logic to determine a deviation between current lung volume and a desired target lung volume, and, in turn, an appropriate adjustment to one or more stimulation parameters (e.g., frequency, power, voltage, etc.). The plot 1220 shows various changes in stimulation power that aim to reduce error between a control result and an intrinsic target, as illustrated by the control result and the intrinsic target of the plot 1210.

In accordance with the example of FIG. 12, an exemplary method includes controlling inspiration for a set number of inspirations using a closed-loop controller that relies on one or more adjustable stimulation parameters, recording values for the one or more adjustable parameters, determining an average value for each of the one or more adjustable parameters, and controlling inspiration based at least in part on the average value for each of the one or more adjustable parameters. Such an exemplary method optionally relies on a forgetting factor or a moving average to control inspiration. For example, such an exemplary method may update an average on a first in, first out basis (FIFO) wherein the average is based on a set number of controlled inspirations. In another example, a forgetting factor is used that weighs more recent data more heavily than older data. In general, such control algorithms typically aim to learn over time or over a set number of inspirations. Further, one or more learned parameter values may optionally be used in an open-loop control scheme that does not rely on sensed information related to inspiration to adjust stimulation during an inspiration.

Figure 13:
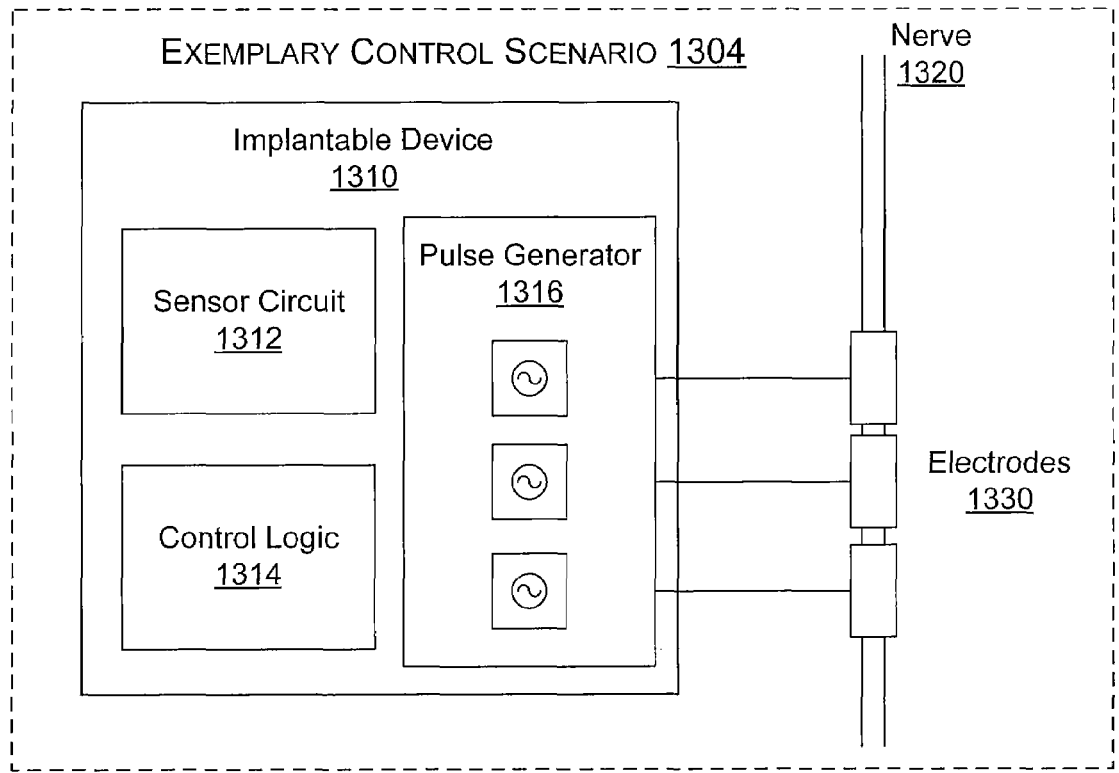
FIG. 13 is a block diagram of various exemplary control scenarios that include a sensor circuit, control logic and a pulse generator.
Figure 13:
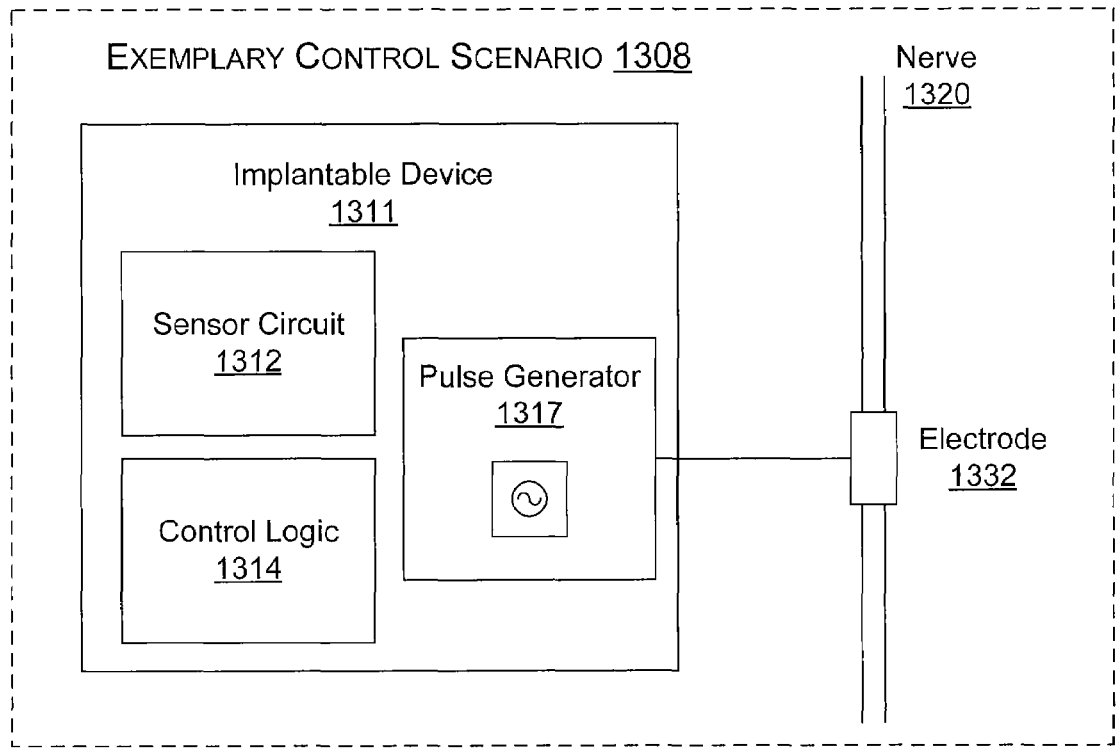

While various exemplary methods discussed herein may be implemented using an implanted device having most of the features of the implanted device 100, FIG. 13 shows exemplary control scenarios 1300 each with an implantable device that includes at least a sensor circuit, control logic and a pulse generator. An exemplary control scenario 1304 includes an implantable device 1310 that includes a sensor circuit 1312, control logic 1314 and a pulse generator 1316, a nerve 1320 and a set of electrodes 1330 positioned on or proximate to the nerve 1320. In this example, the pulse generator 1316 includes a plurality of frequency generators that may deliver stimulation to the nerve 1320 via corresponding electrodes 1330. Thus, referring to the example waveforms of FIG. 8, the exemplary scenario 1304 includes each frequency delivered via one of the corresponding electrodes, all frequencies delivered via one or more electrodes, or other possible combinations of frequencies and electrodes.

Another exemplary control scenario 1308 includes an implantable device 1311 that includes a sensor circuit 1312, control logic 1314 and a pulse generator 1317, a nerve 1320 and an electrode 1332 positioned on or proximate to the nerve 1320. In this example, a frequency generator optionally generates waveforms including one or more component frequencies, which may be applied to the nerve 1320 via the electrode 1332.

Figure 14:
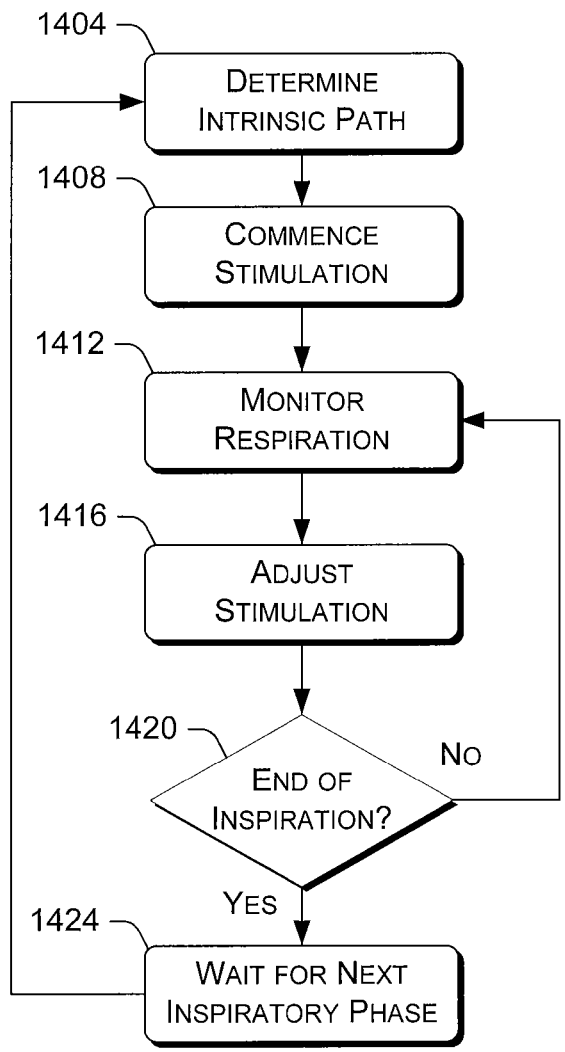
FIG. 14 is a block diagram of an exemplary method for controlling inspiration.

FIG. 14 shows a block diagram of an exemplary method 1400 for controlling respiration. Such an exemplary method is typically implemented once a desire for inspiratory control has been detected. According to the exemplary method 1400, a determination block 1404 determines an appropriate intrinsic inspiratory path. Following the determination, a commencement block 1408 commences stimulation aimed at controlling inspiration. A monitor block 1412 monitors respiration, for example, via sensing. An adjustment block 1416 works in conjunction with monitoring and/or sensing of the monitor block 1412 to adjust stimulation according to control logic as appropriate. A decision block 1420 follows that decides if a set point such as an inspiratory time interval has expired, a maximum lung volume has been reached, etc. If the set point has been reached, then the method 1400 continues in a wait block 1424, which waits for triggering (intrinsically or other) of a subsequent inspiratory phase of respiration. If the set point has not been reached, then the method 1400 continues at, for example, the monitor block 1412.

While various exemplary methods, devices, systems, etc., refer to chest monitoring, or other types of monitoring or sensing information related to inspiration, such sensing or monitoring may employ input such as activity, heart rate, mixed venous $O_2$ concentration, etc. Further while various examples refer to stimulation frequency and voltage, as mentioned, other parameters may be used in addition to or as alternatives to frequency and voltage.

What is claimed is:

1. A method of facilitating inspiration, said method comprising:
   providing an intrinsic inspiratory target;
   delivering stimulation according to one or more stimulation parameters to induce contraction of the diaphragm;
   sensing information related to inspiration induced by the diaphragm contraction;
   determining an error using the intrinsic inspiratory target and the information;

adjusting one or more stimulation parameters based at least in part on the error; and determining an average of the one or more stimulation parameters as a function of time for a plurality of inspirations.

2. The method of claim 1, wherein the intrinsic inspiratory target comprises information on lung volume with respect to inspiratory time.

3. The method of claim 1, wherein the intrinsic inspiratory target comprises information on inspiratory flow with respect to inspiratory time.

4. The method of claim 1, wherein delivering comprises delivering stimulation to a phrenic nerve.

5. The method of claim 1, wherein the one or more stimulation parameters include pulse width.

6. The method of claim 1, wherein the one or more stimulation parameters include frequency.

7. The method of claim 1, wherein the one or more stimulation parameters include voltage.

8. The method of claim 1, wherein sensing comprises monitoring impedance.

9. The method of claim 1, wherein providing comprises providing an intrinsic inspiratory target related to one of a plurality of activity states available for selection.

10. The method of claim 9, wherein the plurality of activity states available for selection comprises at least two of a sleep state, a sitting state, a standing state and an exercising state.

11. The method of claim 1, wherein the adjusting occurs during inspiration.

12. The method of claim 1, wherein delivering comprises delivering a plurality of different waveforms in sequence during inspiration.

13. The method of claim 1 wherein adjusting one or more stimulation parameters based at least in part on the error comprises controlling inspiration based on the average value of each of the one or more stimulation parameters.

14. The method of claim 1 further comprising determining a standard deviation of the one or more stimulation parameters as a function of time for a plurality of inspirations.

15. The method of claim 14 further comprising:

monitoring for one or more stimulation parameters that fall outside the standard deviation; and indicating a change in patient state when one or more stimulation parameters that fall outside the standard deviation.

16. An apparatus for facilitating inspiration, said apparatus comprising:

means for providing an intrinsic inspiratory target;

means for delivering stimulation according to one or more stimulation parameters to induce contraction of the diaphragm;

means for sensing information related to inspiration induced by the diaphragm contraction;

means for determining an error using the intrinsic inspiratory target and the information;

means for adjusting one or more stimulation parameters based at least in part on the error; and means for determining an average of the one or more stimulation parameters as a function of time for a plurality of inspirations.

\* \* \* \* \*